United States Patent [19]

Lorenz

[11] Patent Number: 5,264,519
[45] Date of Patent: Nov. 23, 1993

[54] PROCESS FOR PREPARING POLYURETHANES WITH 4,4'-(ω-HYDROXYALKOXY)-BIPHENYLS

[75] Inventor: Otto Lorenz, Aachen, Fed. Rep. of Germany

[73] Assignee: Bayer Aktiengesellschaft, Leverkusen, Fed. Rep. of Germany

[21] Appl. No.: 986,835

[22] Filed: Dec. 9, 1992

Related U.S. Application Data

[62] Division of Ser. No. 652,345, Feb. 7, 1991, abandoned.

[30] Foreign Application Priority Data

Feb. 14, 1990. [DE]  Fed. Rep. of Germany ... 4004493

[51] Int. Cl.$^5$ .............................................. C08G 18/32
[52] U.S. Cl. .......................................... 528/79; 528/85
[58] Field of Search ................................ 528/79, 85

[56] References Cited

U.S. PATENT DOCUMENTS

| | | | |
|---|---|---|---|
| 2,140,824 | 12/1938 | Vernon | 568/643 |
| 2,789,965 | 4/1957 | Reynolds et al. | 528/86 |
| 3,078,257 | 2/1963 | Rinke et al. | 528/79 |
| 3,562,335 | 2/1971 | Gildersleve | 568/643 |
| 4,170,711 | 10/1979 | Orlando | 568/610 |

FOREIGN PATENT DOCUMENTS

| | | | |
|---|---|---|---|
| 44-880 | 1/1969 | Japan | 528/79 |
| 57-92060 | 6/1982 | Japan | 528/79 |
| 57-109867 | 7/1982 | Japan | 528/79 |
| 1019566 | 2/1966 | United Kingdom . | |

OTHER PUBLICATIONS

Japan Patent Abstract No. 61-68436, vol. 10, No. 235, Aug. 14, 1986.
D. Dietrich in Houben-Weyl: Methoden der Organischem Chemie, vol. E 20, pp. 1568-1571 and 1629-1641; G. Thieme Verlag, Stuttgart, 1987.
B. Reck et al., Makromol. Chem. Rapid, Comm. 6, (1985), 291.

*Primary Examiner*—John Kight, III
*Assistant Examiner*—Rabon A. Sergent
*Attorney, Agent, or Firm*—Joseph C. Gil; Godfried R. Akorli

[57] ABSTRACT

The present invention discloses new compounds of the formula 4,4'-di-(ω-hydroxyalkoxy)-biphenyl wherein the alkoxy group contains from 8 to 13 carbon atoms. The use of the new compounds, in particular the compound 4,4'-di-11-hydroxyundecanoxy)-biphenyl, in the synthesis of segmented polyurethanes, results in products having a particularly advantageous profile of properties.

3 Claims, No Drawings

PROCESS FOR PREPARING POLYURETHANES WITH 4,4'-(ω-HYDROXYALKOXY)-BIPHENYLS

This application is a division of application Ser. No. 07/652,345 filed Feb. 7, 1991 now abandoned.

BACKGROUND OF THE INVENTION

1. Field of the Invention

This invention relates to new compounds which are hydroxybiphenyls. More specifically, the invention relates to hydroxyalkoxybiphenyls of the formula 4,4'-di-(ω-hydroxyalkoxy)-biphenyls wherein the alkoxy moiety contains 8–13 carbon atoms, in particular 4,4'-di-(11-hydroxyundecanoxy)-biphenyl (I), and to their preparation and use in the preparation of segmented polyurethanes.

2. Brief Description of the Prior Art

The compounds of this invention have not hitherto been known. They may be prepared by processes which are analogous to known processes, e.g. from the reaction of 4,4'-dihydroxybiphenyl and ω-halogenalkanols (halogen=Cl, Br) (see e.g. B. Riek et al, Makromol. Chem. Rapid. Comm. 6 (1985), 291).

It was surprisingly found that the compounds of this invention, in particular (I), are valuable components for the synthesis of segmented polyurethanes. The polyurethanes obtained from them by known processes (see e.g. D. Dieterich in Houben Weyl: Methoden der Organischen Chemie, Volume E 20, pages 1568–1571 and 1629–1641; G. Thieme Verlag, Stuttgart 1987) differ advantageously from analogously structured polyurethanes containing, for example, butane-1,4-diol or the known 4,4'-di-(ω-hydroxyalkoxy)-biphenyls such as the corresponding hexane or propane compounds.

SUMMARY OF THE INVENTION

In accordance with the foregoing, the present invention encompasses a new compound of the formula 4,4'-di-(ω-hydroxyalkoxy)-biphenyl wherein the alkoxy group contains from 8 to 13 carbon atoms.

The use of the new compounds, in particular the compound 4,4'-di-(11-hydroxyundecanoxy)-biphenyl, in the synthesis of segmented polyurethanes, instead of the widely used compounds such as butane-1,4-diol, results in polyurethane products having a particularly advantageous profile of properties. In the preparation of the polyurethanes, the new compounds are reacted with polyisocyanates which are generally known.

In particular, the polyurethane products are found to have high tension values as well as thermal transitions which indicate the presence of well-developed mesophases, i.e. liquid crystalline phases. It would appear that an advantageous decoupling of mesogenic region and urethane moiety takes place due to the great spacer length, i.e. a flexible piece of chain by which it is possible to keep the urethane moiety solid, whereas the mesogenic region liquifies to form a mesophase.

Additional chemical cross-linking below the thermal transition point leads to a further improvement in the mechanical properties of elongation. Melamine resins, for example, are suitable cross-linking agents.

DETAILED DESCRIPTION OF THE INVENTION

The present invention will now be described in more detail with the aid of the following non-limiting examples.

EXAMPLE 1

Preparation of 4,4'-di-(11-hydroxyundecanoxy)-biphenyl (I)

Starting materials:
4,4'-dihydroxybiphenyl (DHB)

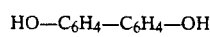

KOH pellets
11-bromoundecanol (Br-(CH$_2$)11—OH).
Solvent: Ethanol.
Apparatus: 500 ml three-necked round bottomed flask, stirrer, contact thermometer, mushroom heating hood, reflux condenser.

0.054 Mol (10 g) of DHB and 0.12 mol (6.8 g) of KOH were dissolved in 200 ml of ethanol.

0.12 Mol (30.15 g) of 11-bromoundecanol were then added and the reaction mixture was heated under reflux for 16 hours.

The solution obtained was poured into 1 liter of distilled water.

The precipitate was separated by suction filtration and washed with 50 ml of 0.1N NaOH and then washed with distilled water until it became neutral.

After the precipitate had been dried, it was recrystallized twice from a mixture of ethanol and tetrahydrofuran in a volumetric ratio of 5/3. Yield: about 50%, m.p.: 159° C.

EXAMPLES 4–5 AND COMPARISON EXAMPLES 2–3

Synthetic segmented polyurethanes

The 4,4'-di-(ω-hydroxyalkoxy)-biphenyl (herein represented as DO) component was stirred into the dehydrated macrodiol at about 80° C. but did not dissolve completely therein. The diisocyanate (DI) was also introduced dropwise with stirring at 80° C. and the mixture was then slowly heated to 110° C. When isophorone diisocyanate (IPDI) or mixtures of IPDI and hexamethylene diisocyanate (HDI) (with IPDI as the main component) were used, a clear solution formed within one hour when 3-DO was used; when 6-DO or 11-DO was used, an addition of N-methylpyrrolidone (NMP) (10–20%, based on the total mass) was necessary for obtaining a clear solution. (The numbers 3, 6, and 11 represent the number of methylene groups). When HDI was used as the only DI, clear solutions were in all cases obtained only after the addition of NMP. Polycaprolactone (PCL) was found to be better than poly(tetramethylene oxide) (PTMO) for the formation of clear solutions. The isocyanate (NCO) conversion was monitored by titration. The reaction time for the formation of the prepolymer of the isocyanate was generally 3 hours at 110° C. After cooling to about 80° C., the isocyanate prepolymer was dissolved in anhydrous tetrahydrofuran (THF) so that the solids content was 30 to 35%.

When 1,3-diaminopropane or N-methyl-1,3-diaminopropane was used for chain lengthening, the solution of isocyanate prepolymer (solvent: THF or a mixture of THF and NMP) was stirred into a 2.5% solution of the diamine in THF.

Non-ionic polyurethanes, formulations, DSC (Differential Scanning Calorimetry) events and mechanical properties.

| Starting materials | 2 | 3 | 4 | 5 |
| --- | --- | --- | --- | --- |
| PTMO 2000[b]/mol | — | — | — | — |
| PCL 1250[a]/mol | 0.8 | 0.8 | 0.8 | 0.6 |
| BD[a]/mol | 0.6 | — | — | — |
| 6-DO[a]/mol | — | 0.6 | — | — |
| 11-DO[a]/mol | — | — | 0.6 | 0.6 |
| HDI[a]/mol | 0.4 | 0.4 | 0.4 | 0.4 |
| 1,3-DAP[b]/mol | 1.6 | 1.6 | 1.6 | 1.6 |
| N-Me-1,3-DAP[b]/mol | — | — | — | 1.2 |
| $T_g$/K | 231 | 231 | 226 | 226 |
| $T^c$/K (heating) | *(320) | *(320) | *(326) | *(326) |
|  | — | — | 357 | 354 |
|  | — | — | 396 | 398 |
|  |  |  | *(417) |  |
| $T^c$/K (cooling) |  |  | 339 | 337 |
| $50^d$/Ncm$^{-2}$ |  |  |  |  |
| (20° C.) | 95 | 135 | 345 | 335 |
| (40° C.) | 75 | 70 | 270 | 195 |
| (60° C.) | 55 | 30 | 130 | 65 |
| (80° C.) | n.m. | n.m. | n.m. | n.m. |

[a] HDI = 1,6 hexamethylenediisocyanate; BD = 1,4-butanediol; 3-DO, 6-DO, 11-DO = 4,4-di-(ω-hydroxy-alkoxy)-biphenyl having 3, 6 or 11 methylene groups; PCL = poly(caprolactone); Mn = 1250 g/mol; IPDI = 3-isocyanatomethyl-3,5,5-trimethyl-cyclohexyl isocyanate which is commonly referred to as isophorone diisocyanate.
[b] PTMO 2000 = poly(tetramethylene oxide), $\overline{M}_n$ = 2000 g/mol; 1,3-DAP = 1,3-diaminopropane; N-Me-1,3-DAP = N-methyl-1,3-diaminopropane.
[c] Thermal events of the second heating up and cooling down process.
[d] Tension values at 50% elongation.
$\overline{M}_n$ average molecular mass (average by nubmer).
*Thermal events of not clearly defined temperature.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of preparing a polyurethane comprising reacting a polyisocyanate with a compound of the formula 4,4'-di-(ω-hydroxyalkoxy)-biphenyl wherein the alkoxy moiety contains from 8 to 13 carbon atoms.

2. A polyurethane which is prepared by the method of claim 1.

3. A method of claim 1 wherein the compound is 4,4'-di-(11-hydroxyundecanoxy)-biphenyl.

* * * * *